United States Patent [19]

Capco et al.

[11] Patent Number: 4,983,527
[45] Date of Patent: Jan. 8, 1991

[54] OOCYTE TEST FOR DETECTION OF TUMOR PROMOTING COMPOUNDS

[75] Inventors: David G. Capco; William M. Bement, both of Tempe, Ariz.

[73] Assignee: Arizona Board of Regents, Tempe, Ariz.

[21] Appl. No.: 357,704

[22] Filed: May 26, 1989

[51] Int. Cl.$^5$ .......................... C12N 1/00; C12P 1/00; G01N 33/483

[52] U.S. Cl. .................................. 436/63; 435/172.1; 435/240.1; 435/240.2; 436/64; 436/813

[58] Field of Search .......................... 436/63, 64, 813; 435/240.1, 240.2, 68, 29, 172.1, 948

[56] References Cited

U.S. PATENT DOCUMENTS

| | | | |
|---|---|---|---|
| 4,262,090 | 4/1981 | Colby, Jr. et al. | 435/68 |
| 4,359,527 | 11/1982 | Zetter | 435/29 |
| 4,465,769 | 8/1984 | Hampar et al. | 435/948 |
| 4,486,538 | 10/1984 | Bogoch | 436/503 |
| 4,569,916 | 2/1986 | Penman et al. | 436/64 |
| 4,675,288 | 6/1987 | Falck | 435/29 |
| 4,701,406 | 10/1987 | Chou | 436/63 |

OTHER PUBLICATIONS

"Protein Kinase C as the Receptor for the Phorbol Ester Tumor Promoters: 6th Rhoads Memorial Award Lecture", Blumberg, P. M., Cancer Res. 48:1-8 1988.
"Analysis of Proteins in the Peripheral and Central Regions of Amphibian Oocytes and Eggs", Capco, D. G. and Mecca, M. D. Cell Differ. 23:155-164 1988.
"Direct Activation of Calcium-Activated, Phospholipid-Dependent Protein Kinase by Tumor Promoting Esters", Catagna et al J. Biol. Chem. 257:7847-7851 1982.
"Protein Incorporation by Isolated Amphibian Oocytes. III Optimum Incubation Conditions", Wallace et al. J. Exp. Zool. 184:321-334 1973.
"Activators of Protein Kinase Trigger Cortical Granule Erocytosis, Cortical Contraction & Cleavage Furrow Formation . . . " Bement & Capco Jour. Cell Bio. Mar. 1989.
"Identification of Microtubule-Associated Proteins (MAPS) in Xenopus Oocytes" Jessus, Thiber & Ozon FEBS Lett. 192(1) 135-40.
"A Freeze-Sectioning Method for Preparation of the Detergent-Resistant Cytoskeleton . . . Embryos" Hampton, Perry & Capco. Dev. Growth Differ.
"Molecular Biology of the Cell" Aberts et al. p. 294 © 1983 Garland Publishing Inc., New York, NY.

Primary Examiner—Robert J. Warden
Assistant Examiner—Robert J. Trautman
Attorney, Agent, or Firm—Richard R. Mybeck

[57] ABSTRACT

A unique, quick, inexpensive and highly accurate assay for detecting the presence of tumor promoters based on a measurable set of changes in amphibian oocytes in the presence of a tumor promoter. A secondary assay based on the protein released by the oocytes is employed to confirm the initial assay and quantify the potency of the tumor promoter present.

14 Claims, 2 Drawing Sheets

OOCYTE TEST FOR DETECTION OF TUMOR PROMOTING COMPOUNDS

INTRODUCTION

The present invention relates to an assay for determining whether a composition is a tumor promoter or has tumor promoting activity as part of its carcinogenic action.

BACKGROUND OF THE INVENTION

Tumor promoters are those compositions that effect the formation of tumors in those cells that have been previously initiated. Initiation is an event which appears to damage the DNA of cells, but does not necessarily result in tumor formation. Exposure of initiated cells to promoting agents leads to carcinomas and papillomas. Prior to the present invention, there has been no simple, quick and inexpensive test for determining whether a composition is a tumor promoter or has tumor promoting activity. One existing test involves painting mouse skin with suspected compositions. Demonstration of promoting activity requires repeated application of the composition over several months before carcinomas and papillomas are detected. This analysis is expensive and time consuming.

A second category of compositions are known as complete carcinogens. These are capable of inducing tumors by themselves without the prior requirement of exposure to initiators or treatment with the promoters. Such compositions appear to combine both initiating and promoting activity. Prior to the present invention, compositions to which humans are exposed, such as food additives, topical products, or the like, must be routinely tested to determine their activity for causing cancer in humans. Long term tests for carcinogenic compositions expose animals to suspected compositions and measure tumor formation. Such tests are labor intensive, expensive and produce variable results. A widely used short-term test, and one that does not require animal testing, is known as the Ames test. This test is of limited utility and can only determine whether a composition damages DNA sufficiently to result in mutagenesis. The Ames test cannot measure tumor-promoting activity of compositions nor detect that activity of a carcinogen which is not mutagenic. The Ames test involves the activation of a composition using a microsomal extract from rat liver. The activated composition is mixed with a bacterial strain bearing a mutation. Mutagenic compounds are detected by their ability to reverse the mutation, thereby allowing the bacteria to grow in a restrictive medium. Thus, carcinogens are identified on the basis of their ability to induce specific mutations.

While most complete carcinogens cause mutagenesis, not all mutagens are complete carcinogens. Furthermore, the Ames test is not capable of determining whether a composition is a tumor promoter. For example, the Ames test is not capable of determining which components of tobacco smoke are tumor promoters nor can it detect the tumor promoting activity of dioxin (TCDD). Thus, the Ames test is seriously deficient, since both dioxin and tobacco smoke are well known tumor promoting agents common in the environment.

Thus, the need persists for an accurate, inexpensive and definitive short-term test for determining whether a particular composition is a tumor promoter or has tumor promoting activity. Such a test should also establish whether a known mutagen has promoter activity and therefore is apt to behave as a complete carcinogen. Furthermore, it would be desirable to provide a test which is capable of making such a determination directly at extremely low dilutions in the order of one part per billion or less.

If a simple and inexpensive, yet highly accurate assay could be provided to identify the presence of tumor promoters, an important tool in the prophylaxis and management of cancer would be provided.

One such prior art attempt at such an assay was developed by Penman et al and is described in U.S. Pat. No. 4,569,916 which issued Feb. 11, 1986. While representing a major step forward in the context of the times, the assay described therein suffered from the fact that it was dependent upon $20,000 to $30,000 of equipment and required several hours to complete.

Accordingly, a need still exists for the development of an accurate, quick and inexpensive assay for the detection of tumor promoters and tumor promoting activity and it is toward this goal that the present invention is directed.

BRIEF SUMMARY OF THE DISCLOSURE

The present invention is predicated upon the discovery of a unique, quick, inexpensive and highly accurate assay for detecting the presence of tumor promoters in a physiological system.

The assay specifically identifies the presence of tumor promoters on the basis of their propensity to induce a readily measurable set of changes in *Xenopus laevis* oocytes. Specifically, the present invention is predicated upon the unexpected discovery that tumor promoters cause oocytes to release protein from specialized cortical granules beneath the surface of the oocyte and at the same time, undergo surface contraction. The surface contraction of each oocyte usually occurs within 10–30 minutes after its exposure to the tumor promoter and results in a profound alteration of oocyte surface pigmentation which can be readily observed with the naked eye.

Thus, unlike those assays for tumor promoters heretofore known which are time-consuming, expensive and require a significant amount of scientific expertise and equipment to perform, the oocyte assay of the present disclosure is extremely rapid (10–30 minutes) and requires only the ability and the equipment necessary for oocyte preparation and observation. The only supplies required are female frogs, surgical tools, Petri dishes and oocyte media, all at a cost of less than $1,000.00. A dissecting microscope can facilitate the assay and is available for about $2,000.00.

In addition to visual observation of the oocyte surface which allows rapid detection of nanomolar concentration of tumor promoter, the sensitivity of the oocyte assay can be extended by other techniques which are readily available in virtually any biological laboratory. For example, oocyte protein release from cortical granules can be monitored by simple spectrophotometry for more precise, quantitative analysis of tumor promoting activity and for a measure of an unknown's tumor promoting ability. A still further level of sensitivity can be obtained by using electron microscope analysis of the treated oocytes to count the relative number of remaining cortical granules.

Accordingly, the principal object of the present invention is to provide a new and improved assay for the detection of tumor promoting agents which is reliable, quick and inexpensive to perform.

Another object of the present invention is to provide a novel and unique assay for the detection of tumor promoting agents which can be performed in thirty minutes or less and evaluated by the unaided human eye.

Still a further object of the present invention is to provide an inexpensive, quick and accurate initial assay employing oocytes to identify the presence of tumor promoters and a readily performed confirmatory measurement using the absorbance of the media containing the oocytes to quantify the relative potency of the tumor promoter.

These and still further objects as shall hereinafter appear are fulfilled by the present invention in a remarkably unexpected manner as shall be readily discerned from a careful consideration of the following detailed description of exemplary embodiments thereof especially when considered in conjunction with the accompanying drawings.

DESCRIPTION OF PREFERRED EMBODIMENTS

Figure 1:
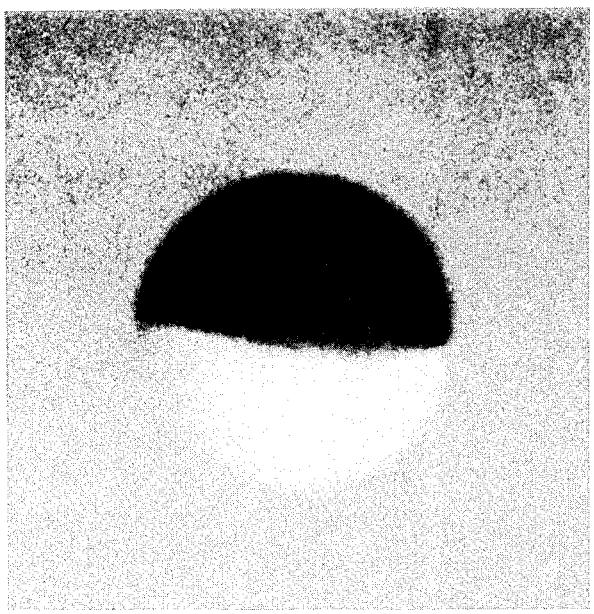
FIG. 1 is a photomicrograph taken from the side of an oocyte prior to treatment with a tumor promoting substance.

In one practice of the present invention preparation includes obtaining Xenopus oocytes from the excised ovaries of female *Xenopus laevis* anesthetized by hypothermia and from which follicle cells have been removed by treatment for one hour with one percent (1%) collagenase. After collagenase treatment, the full grown oocytes (1.1–1.4 mm) are isolated, washed extensively, and incubated in plastic Petri dishes about four to about six hours in 1×O-R2. After 4–6 hours, the oocytes are transferred to clear plastic Petri dishes containing fresh O-R2. The follicle cells adhered to the Petri dishes and were removed as a complete sheath by pushing the oocytes across the Petri dish with forceps.

The assay begins by incubating the oocytes in a suitable media, preferably a simple salt solution known to the art as O-R2, containing small quantities of the unknown being assayed for the presence of tumor promoters or tumor promoting activity. The oocytes are thereafter evaluated by eye for profound pigmentation changes which characterize the presence of tumor promoters.

As can be observed from the drawing, the contraction of the oocyte surface which occurs in response to contact with tumor promoters is readily illustrated with the aid of a dissecting microscope. As shown in the accompanying photomicrographs, the effect of tumor promoters on oocytes is profound.

Figure 2:
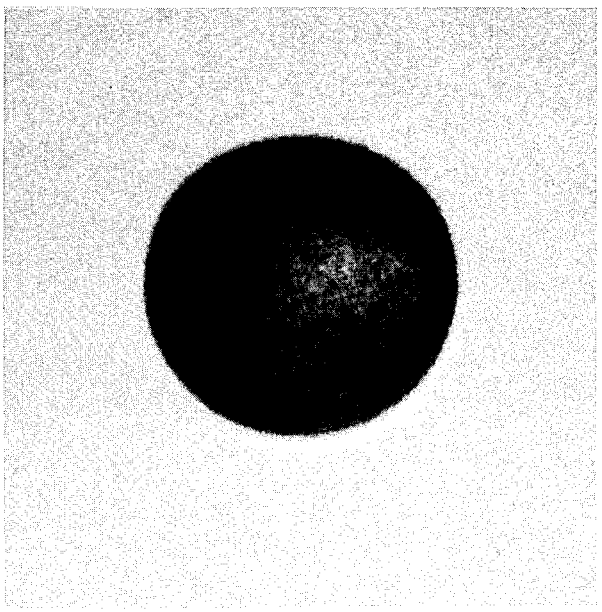
FIG. 2 is a photomicrograph taken from the top of an oocyte prior to treatment.

Referring to FIG. 1, prior to treatment with a known tumor promoting substance, the oocyte has a light-colored hemisphere and a dark-colored hemisphere which occupy essentially the same amount of surface area when viewed from the side. When the unexposed oocyte is viewed from the top as shown in FIG. 2, only the dark-colored hemisphere is visible.

Figure 3:
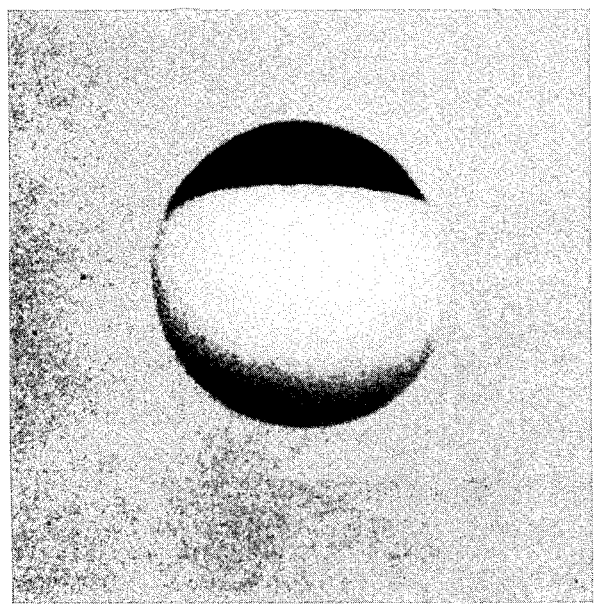
FIG. 3 is a photomicrograph taken from the side of an oocyte after treatment with a known tumor promoter.

After treatment with a tumor promoter, the oocyte surface contracts vigorously with the surface area of the light-colored hemisphere increasing dramatically in size at the expense of the surface area of the dark-colored hemisphere as shown in FIG. 3.

Figure 4:
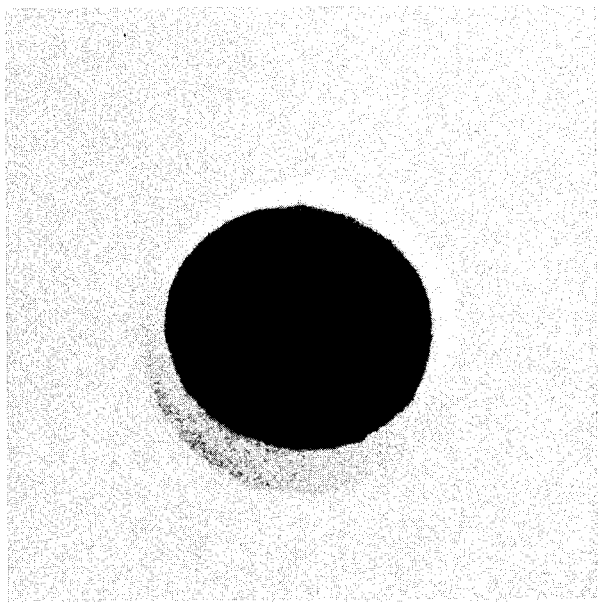
FIG. 4 is a photomicrograph taken from the top of an oocyte after treatment with a known tumor promoter.

When the same treated oocyte is viewed from the top as shown in FIG. 4, the dark-colored hemisphere becomes much darker than it was as an untreated oocyte (Cf. FIG. 2) and the light-colored hemisphere has expanded to where it is now visible as a circle circumscribing the dark-colored hemisphere.

O-R2, referred to above, is made of distilled water and a number of off-the-shelf chemicals; namely, sodium chloride, potassium chloride, sodium phosphate, sodium hydroxide, magnesium chloride, calcium chloride and HEPES.

In a preferred practice, the chemicals are added to a bath of distilled water to provide the following concentrations:

| | |
|---|---|
| Sodium chloride | 82.5 mM |
| Potassium chloride | 2.5 mM |
| Sodium phosphate | 1.0 mM |
| Sodium hydroxide | 3.8 mM |
| Magnesium chloride | 1.0 mM |
| Calcium chloride | 1.0 mM |
| HEPES | 5.0 mM |

After the foregoing chemicals are added to the distilled water in the concentrations shown above, the pH of the medium is adjusted to 7.4 by the addition of hydrochloric acid.

It is of course understood that any of the various media normally employed to maintain frog oocytes in the laboratory can be used herein in lieu of the O-R2 medium with equally satisfactory results.

To further aid in the understanding of the present invention and not by way of limitation, the several facets that make up a successful assay will now be described.

Sample Preparation

The substance to be tested for the existence of tumor promoting activity will either be solid or liquid. If solid, the substance will be dissolved in O-R2 or an equivalent medium to provide a series of concentrations at: 1%, 0.1% and 0.01%. If the substance is liquid, it will be diluted in O-R2 or an equivalent medium to provide a concentration series of: 1%, 0.1% and 0.01%. Note that when the substance to be tested is in a water-based solution, it can be first lyophilized to concentrate the substance into a powder and then dissolved in the selected medium.

Initial Assay

A batch of 120 oocytes obtained from a single frog are divided into six groups containing 20 oocytes each. Three groups will function as controls for the assay and three groups will function as unknowns. Of the three control groups, two provide negative controls and one provides a positive control.

One negative control, herein denominated Group I, involves incubation of one group of twenty oocytes in O-R2 alone.

Group II, a positive control, involves the incubation of a second group of twenty oocytes in O-R2 which contains a known tumor promoter phorbol myristate acetate (PMA) at a concentration of one micromolar.

Group III, the second negative control, involves incubation of a third group of twenty oocytes in O-R2 which contains a one micromolar concentration of the inactive form of PMA, that is, that form which does not have tumor promoting activity.

Three unknown groups are also established. Group IV comprises a fourth group of twenty oocytes incubated in O-R2 into which has been disposed a 1% concentration of the unknown substance.

Group V is similar to Group IV in that it contains the fifth group of twenty oocytes incubated in O-R2 medium into which has been deposited a 0.1% concentration of the unknown substance.

Group VI likewise contains the sixth group of twenty oocytes for incubation in O-R2 which contains 0.01% of the substance being tested.

Detection of Oocyte Concentration

Tumor promoters have been found to induce a readily discernible effect on oocytes when the tumor promoter and the oocytes are admixed in a medium. Thus, either the natural pigment of the oocyte occupies 50% or more of the oocyte surface area, indicating no effect, or the pigment contracts to occupy 40% or less of the oocyte surface area which signals tumor promoting activity. The reference to percentage of the surface occupied means that portion of the total surface area of the oocyte. The reference to pigment identifies the dark-colored hemisphere as shown in the drawing.

While, as will appear, the contraction of the pigmented animal hemisphere can be readily observed with the unaided eye in a properly lighted room, there will be times when an inexpensive dissecting microscope containing a measuring device will prove extremely helpful in measuring the extent of the contraction. Such an instrument adds only minimal cost to the assay and is, of course, available for use by the technician in other procedures.

After examination, the total number of oocytes which have contracted in each group will be divided by the total number of oocytes in that group. The result will be multiplied by 100 to give a percent reading. For example if in a given group, e.g. Group IV, ten oocytes contract and ten oocytes do not contract, the Group will be rated as having 50% contraction, (i.e., $10/20 \times 100$).

Once the six groups are established, and this can be done virtually simultaneously by adding the oocytes to the medium at the last moment, each Group should be examined every ten minutes during the first hour following admixture, at 30 minute intervals during hours 2 through 4, and then again at 24 hours.

In the operation of the assay, Group II should exhibit 100% contraction within 20-30 minutes from the start of the treatment. The oocytes in the negative control groups, that is, Groups I and III, will exhibit 0% contraction even after 24 hours.

Groups IV, V and VI, which contain the various concentrations of the unknown substance, will, if the test substance has tumor promoting activity, demonstrate some percentage of contraction. Note that any percentage of contraction, no matter how low, is itself evidence of the existence of some tumor promoting activity.

If no contraction is observed in Group IV-VI, the test substance does not have tumor promoting activity. However, if only one oocyte contracts, it is recommended that the assay be repeated with a larger number of oocytes to avoid condemning a substance on what could possibly be an aberration.

Spectrophotometric Assay

In the course of the work which resulted in the assay of the present invention, it was also determined that tumor promoters trigger the release of a specific set of proteins from the oocyte. This protein release can also be measured and/or confirmed using a spectrophotometer which thus forms a basis for confirming the initial assay. The spectrophotometer is a common piece of laboratory equipment which can be used to measure the absorbance of electromagnetic radiation. If a spectrophotometer is not available, one can be obtained for about $5,000-$7,000.

The quantitative data obtained by this portion of the assay enables an operator to precisely determine the relative tumor promoting potency of any given substance.

To further aid in the understanding of the present invention, the following examples are illustrative of oocyte assays, and not as a limitation thereof.

Ninety oocytes are divided into nine groups containing ten oocytes each. Each group of ten oocytes receives a different treatment and will function as a control for the assay.

The several treatment groups are constituted as follows: Group I will receive a one-hour incubation in O-R2 alone to provide a first negative control; Group II will receive a six-hour incubation in O-R2 alone to provide a second negative control; Group III will receive a one-hour incubation in O-R2 containing phorbol myristate acetate (PMA), a known tumor promoter, at a concentration of 100 nanomolar to provide a first positive control; Group IV will receive a fifteen minute incubation in O-R2 containing PMA at a concentration of 1 micromolar to provide a second positive control; Group V will receive a one-hour incubation in O-R2 containing the inactive form of PMA at a concentration of 100 nanomolar to provide a third negative control; and Group VI will receive a fifteen minute incubation in O-R2 containing the inactive form of PMA at a concentration of 1 micromolar to provide a fourth negative control.

The unknown to be assayed will be tested at the concentrations or dilutions which gave positive results during the initial assay, that is, at those concentrations which evoked the visible surface contraction. The first specimen is designated Group VII and will receive a 15-minute incubation in O-R2 containing the substance being assayed at a first concentration. Group VIII will be constituted the same as Group VII with respect to medium, unknown and concentration and will receive a one-hour incubation and Group IX will likewise be constituted the same as Group VII and VIII but will receive a six-hour incubation.

Each group is incubated in one milliliter of the indicated medium for the indicated amount of time. At the end of the incubation period, the container with the oocytes still in it is gently agitated. One-half milliliter of the contents of each container is then removed and deposited in a spectrophotometric cuvette. The cuvette is then placed in the spectrophotometer and the absorbance of the medium at 280 nanometers is measured and recorded. If the compound being tested perchance absorbs in the range of 280 nanometers, protein release will have to be measured another way such as by any of the commercially available Protein Assay kits (e.g., BCA Protein Assay Kit, Pierce Chemical Company, Rockford, Ill.). The absorbance at 280 nonometers on the spectrophotometer is then compared with absorbance obtained when a cuvette containing only O-R2 and the unknown is placed in the spectrophotometer. If the absorbance of the experimental medium (containing oocytes) is higher than that of plain O-R2 containing the unknown but no oocytes, protein has been released into and is present in the experimental medium.

The expected results of the foregoing assay for detecting protein release would find little or no protein release in the negative control groups (I, II, V and VI) and a substantial amount of protein released in the positive control groups (III and IV). If the substance being tested is a tumor promoter, protein release should be found in one or more of the test groups (VII, VIII and IX).

One precaution to be taken with the foregoing corroborative assay is to carefully examine the oocytes under a dissecting microscope at the end of each incubation period to assure that none of the oocytes have ruptured. A ruptured oocyte will release protein nonspecifically into the medium and could give a false positive test result.

Spectrophotometry can also be used to obtain quantitative data, that is, data which permits the assayer to precisely determine the relative tumor-promoting potency of a given substance as well as the relative amount of a given tumor promoting substance in a given sample.

This quantitative procedure involves dividing eighty oocytes into eight groups containing ten oocytes each. Positive and negative controls are established as before, namely by depositing ten oocytes in O-R2 alone, in O-R2 with one micromolar of an active form of PMA; and in O-R2 with one micromolar of the inactive form of PMA.

The test groups are created by diluting the unknown in a number of containers of O-R2 to provide a concentration series which brackets the concentration or dilution which gave the highest percentage of surface contraction in the initial assay.

To illustrate, if the concentration which gave the highest percentage of surface contraction in the initial assay was 0.1%, the concentration series here should comprise five (5) test groups of oocytes in O-R2 containing the unknown at concentrations of: 1%, 0 5%, 0.1%, 0.05% and 0.01%, respectively.

The protein release is measured by placing ten oocytes in the bottom of a spectrophotometric cuvette and placing 0.5 ml of the appropriate solution on top of them. Each cuvette is agitated once gently and then placed in the spectrophotometer. The absorbance at 280 nanometers is measured immediately. Note that if the unknown perchance absorbs in the 280 nanometer range, a secondary protein test will be necessary as described above.

Every two minutes thereafter for at least 40 minutes or longer, several hours if necessary, the cuvette is withdrawn from the spectrophotometer, agitated, replaced in the spectrophotometer, and the absorbance at 280 nanometers is measured again. At the end of the test period, the oocytes must be examined to assure that none have ruptured.

To obtain a measure of the rate of protein release, absorbance is plotted against time. If an increasing amount of protein is released over time, the absorbance will increase over time. The precise amount of protein release can be calculated by using a calibration curve prepared by using a known protein standard.

In the operation of the foregoing assay, the negative control should generate a plot where absorbance is low and shows little or no change over time. The positive control group should result in a plot in which the absorbance increases rapidly and then reaches a plateau at about 20 minutes.

Figure 5:
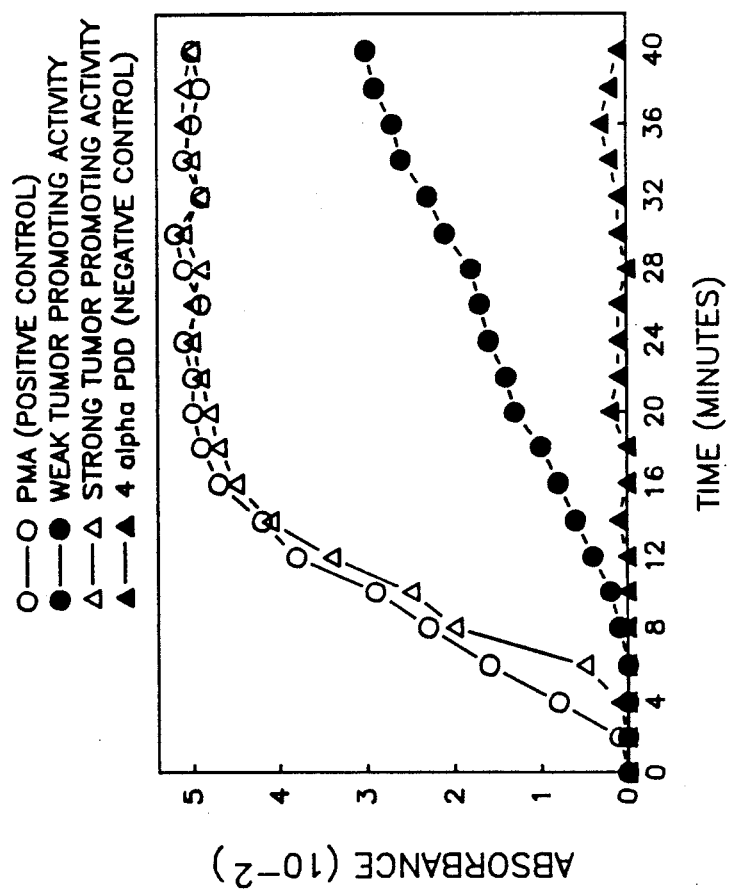
FIG. 5 is a chart showing absorbance versus time for different test samples derived using the present invention.

If the substance being tested has potent tumor promoting activity, one or more of the plots generated using the different concentrations should have a rapid increase of absorbance followed by a plateau at about 20 minutes. If the substance being tested is a less potent tumor promoter, the plots generated for the different concentrations of the substance should exhibit a more gradual increase of absorbance over time. A typical plot of such data is shown in FIG. 5.

The quantitative assay enables the assayer to determine which among two or more samples contains the greater amount of tumor promoting activity and, when a substance of known molecular weight is being tested for tumor promoting activity, the relative tumor promoting potency of that substance.

It is apparent from the foregoing that highly useful initial and corroborative assays have been herein described and illustrated which can be used to screen new products for tumor promoting activity and which will enable government and industry to easily detect the presence of harmful substances in drinking water, produce and other everyday commodities which must be routinely screened to protect the public health. It is, of course, understood that such modification, alterations and adaptations as occur to the artisan when confronted with this disclosure are intended within the spirit of this invention which is limited only by the scope of the claims appended hereto.

Accordingly, what is claimed is:

1. A test for detecting the presence of tumor promoting activity in an unknown substance disposed in a preselected medium, said test comprising the steps of: admixing said unknown substance with a preselected medium to create a medium mixture; depositing said medium mixture on a Petri dish; depositing a controlled number of pretreated amphibian oocytes into said medium mixture on said Petri dish to form an Oocyte-containing medium mixture; incubating said Oocyty-containing medium mixture; measuring the surface contraction of the areas of the animal hemisphere of said oocytes occupied by a dark-colored pigment after said incubation; and comparing said contraction of said dark-colored pigment areas to that obtained by incubating an Oocyte without contact with said unknown substance to determine the percentage of said contraction of said dark-colored pigment area wherein an increase in pigment and an imbalance between the hemispheres is an indication of the presence of a tumor promoting activity.

2. A test according to claim 1 in which said amphibian is frog.

3. A test according to claim 2 in which said frog oocyte is selected from the group consisting of *Xenopus laevis, Xenopus borealis* and *Rana pipiens.*

4. A test according to claim 1 in which said measuring of surface contraction of said oocytes in said oocyte-containing medium mixture is done after about 10 to about 30 minutes of said incubation.

5. A test according to claim 3 in which said oocytes are obtained by first excising ovaries from an anesthetized female *Xenopus laevis* and thereafter treating said oocytes to remove follicle cells therefrom.

6. A test according to claim 5 in which said femal *Xenopus laevis* is anesthetized by hypothermia.

7. A test according to claim 5 in which said excised oocytes are treated with collagenase to remove follicle cells therefrom.

8. A test according to claim 5 in which said follicle cell-free oocytes are isolated, washed, and incubated for about 4–6 hours in 1×O-R2.

9. A test according to claim 8 in which said incubated, follicle cell-free oocytes are transferred to a Petri dish containing fresh O-R2 medium containing said unknown substance.

10. A test according to claim 1 in which said medium consists of a bath of distilled water into which the following reagents are added to provide the following concentrations:

| | |
|---|---|
| sodium chloride | 82.5 mM |
| potassium chloride | 2.5 mM |
| sodium phosphate | 1.0 mM |
| sodium hydroxide | 3.8 mM |
| magnesium chloride | 1.0 mM |
| calcium chloride | 1.0 mM |
| HEPES | 5.0 mM |
| hydrochloric acid | q.s. to provide pH 7.4 |

11. A test according to claim 9 comprising inspecting the incubated oocytes to determine that each is rupture-free; transferring a portion of the medium solution containing rupture-free oocytes and unknown substance to a cuvette; placing the cuvette into a spectrophotometer; and measuring the absorbance of the medium portion at 280 nanometers.

12. A test according to claim 11 comprising concurrently preparing a plurality of cuvettes, each containing a like number of rupture-free oocytes, medium and a different concentration of said unknown substance, measuring the absorbance of each cuvette at 280 nanometers, and plotting the absorbance of each cuvette against the concentration of the unknown substance to provide a quantitative evaluation of the tumor promoting potency of said unknown substance versus the concentration thereof.

13. A test according to claim 5 comprising treating said excised oocytes with calcium-free medium to remove the follicle cells therefrom.

14. A method for confirming the presence of tumor promoting activity in an unknown substance, comprising: removing follicle cells from rupture-free amphibian oocytes; thereafter adding said rupture-free oocytes to a preselected medium to create an Oocyte-containing medium to which said unknown substance is added to form a mixture; placing a portion of said mixture in a cuvette; placing the cuvette in a spectrophotometer; measuring the absorbance of said mixture portion at 280 nanometers; and comparing the absorbance of said mixture portion with the absorbance measured using a known control wherein an increase in absorbance is an indication of the presence of tumor promoting activity.

* * * * *